United States Patent [19]

Photis

[11] 4,234,505

[45] Nov. 18, 1980

[54] PROCESS FOR PREPARING CYANOHYDRIN ESTERS

[75] Inventor: James M. Photis, Ridgefield, Conn.

[73] Assignee: Stauffer Chemical Company, Westport, Conn.

[21] Appl. No.: 80,954

[22] Filed: Oct. 1, 1979

[51] Int. Cl.³ .................. C07C 121/38; C07C 121/46; C07C 121/75

[52] U.S. Cl. .............................. 260/465 D; 260/464; 260/465.4

[58] Field of Search ................ 260/465 D, 464, 465.4

[56] References Cited

U.S. PATENT DOCUMENTS 4,113,763   9/1978   Norton ........................... 260/465 D

FOREIGN PATENT DOCUMENTS 52-142046  11/1977  Japan .

OTHER PUBLICATIONS

Cox et al., *Organic Synthesis Collective* vol. 2, p. 7 (1943).
Wagner et al., *Organic Synthesis Collective* vol. 3, p. 324 (1955).
Nasipuri et al., *J. Indian Chemical Soc.*, 44, 556, (1967).
Gassman et al., *Tetrahedron Letters*, pp. 3773–3776 (1978).
Umino et al., *Tetrahedron Letters*, No. 33, pp. 2875–2876 (1976).
Sugimoto et al., *J. Chem. Soc. Chem. Comm.*, pp. 926–927 (1978).
Kinishi et al., *Agric. Biol. Chem.* 43(4), pp. 869–872 (1978).
Borch et al., *J. Org. Chem.*, 37, pp. 726–729 (1972).

*Primary Examiner*—Dolph H. Torrence
*Attorney, Agent, or Firm*—William C. Gerstenzang

[57] ABSTRACT

Cyanohydrin esters are prepared by forming a mixture of an acyl cyanide, a carboxylic acid anhydride and an alkali metal borohydride and reacting the mixture at a temperature and for a time sufficient to form the cyanohydrin ester product of the acyl cyanide and carboxylic acid anhydride.

14 Claims, No Drawings

PROCESS FOR PREPARING CYANOHYDRIN ESTERS

BACKGROUND OF THE INVENTION

The present invention relates to a novel process for preparing cyanohydrin esters. More particularly, the present invention relates to a novel process for the preparation of cyanohydrin esters which requires neither an aldehyde nor a free cyanohydrin as a starting material and which does not involve the formation of free cyanohydrin compounds as intermediates. Specifically, the present invention relates to a process for the preparation of cyanohydrin esters directly from acyl cyanides.

The cyanohydrin esters are important industrial raw materials in that they provide ready access to highly active insecticides. Thus, for example, it is known to react a cyanohydrin ester, such as meta-phenoxybenzaldehyde cyanohydrin acetate with a chrysanthemate, such as ethyl 3-(2,2-dihalovinyl)-2,2-di-methyl cyclopropane carboxylate to form an insecticide of the pyrethroid type, such as NRDC 149, as follows:

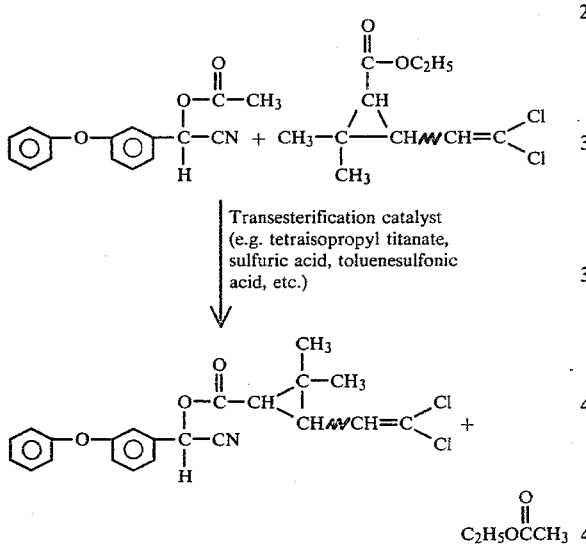

It is known to form cyanohydrin esters by reaction of a cyanohydrin and a carboxylic acid chloride or anhydride, i.e.,:

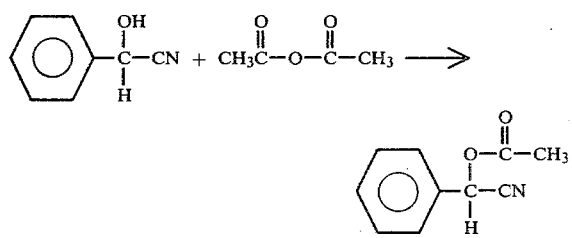

This process, however, requires the use of a free cyanohydrin. The use of free cyanohydrins is objectionable because they are unstable compounds which can release HCN.

Alternatively, it is known to prepare cyanohydrin esters by reacting an aldehyde with an acid chloride in the presence of potassium cyanide, as follows:

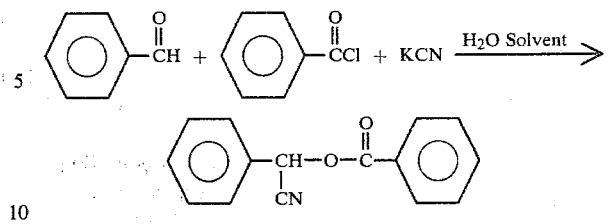

This process avoids the handling of free cyanohydrins, and therefore is not as objectionable as the previously mentioned process. It does, however, require the use of an aldehyde. Aldehydes, while not as objectionable as free cyanohydrins from a handling point of view, can be somewhat difficult to obtain and are relatively expensive.

In yet a third process, disclosed in U.S. Pat. No. 4,113,763, cyanohydrin esters are prepared by reacting an aromatic aldehyde with an aliphatic anhydride and then reacting the product with an alkali metal cyanide. This process, however, also requires the use of an aldehyde starting material.

Therefore a need exists for a novel process for preparing cyanohydrin esters which requires the use of neither a free cyanohydrin nor an aldehyde as a starting material, and which does not involve the formation of a free cyanohydrin as an intermediate compound.

SUMMARY OF THE INVENTION

It is an object of the present invention to provide a novel process by which cyanohydrin esters may be prepared without the use of free cyanohydrin or aldehyde starting materials and without the formation of free cyanohydrin intermediate compounds.

It has now been discovered that cyanohydrin esters may be readily prepared by the reaction of an acyl cyanide with sodium borohydride and an anhydride. Surprisingly and unexpectedly, it has been found that when an acyl cyanide is reduced by an alkali metal borohydride, only the acyl functionality is reduced, and the nitrile moiety remains intact and is not cleaved from the molecule. This is particularly surprising in view of the tendency of other reducing agents, such as lithium aluminum hydride, to also reduce the nitrile functionality and the tendency of other basic reagents, such as sodium hydroxide, to cleave the cyano group from the molecule.

In accordance with the process of the present invention there is provided a process for the preparation of cyanohydrin esters which comprises forming a reaction mixture of an acyl cyanide, an anhydride and an alkali metal borohydride and reacting the reaction mixture at a temperature and for a time sufficient to form the cyanohydrin ester product of the acyl cyanide and anhydride.

Particularly preferred cyanohydrin esters which are prepared in accordance with the present invention are meta-phenoxybenzaldehyde cyanohydrin acetate, benzaldehyde cyanohydrin acetate and meta-phenoxybenzaldehyde cyanohydrin dichlorochrysanthemate.

The chemical reaction of the process of the present invention may be illustrated as follows:

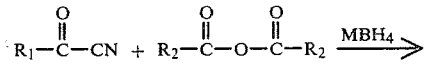

-continued $$O-\overset{O}{\overset{\|}{C}}-R_2$$
$$R_1-\overset{|}{\underset{H}{C}}-CN$$

wherein $R_1$ represents an alkyl, alkenyl, cycloalkyl, aryl, aralkyl, alkylphenyl, diphenyl ether, polyphenyl or heterocyclic radical or a radical made up of any combination thereof; each of which may contain an inert substituent such as halogen, alkyl or alkoxy; $R_2$ represents an alkyl, aryl or cycloalkyl group each of which may contain an inert substituent such as halogen, alkyl, alkenyl, alkoxy or any combination of them; and M represents an alkali metal, preferably sodium or potassium. $R_1$ can have from 1 to about 30 carbon atoms, although 1–15 carbon atoms are preferable. $R_2$ is preferably an aliphatic radical and can have from 1 to about 30 carbon atoms, although 1 to about 10 carbon atoms are preferable.

The reaction mixture may be prepared by dissolving the acyl cyanide in the anhydride, and then stirring-in the alkali metal borohydride. The reaction will begin as soon as all three components are brought together and no special catalysts or temperature conditions will be required, although the reaction mixture should be continuously agitated.

The anhydride will, in general, be in liquid form and serves the dual function of reactant as well as solvent for the acyl cyanide. Where the anhydride being used is a solid at ambient temperatures, it may be desired to use an inert solvent in which both the anhydride and acyl cyanide are soluble. Such inert solvents include, but are not limited to ethers, polyethers, cyclic ethers and the like.

Aqueous solvents can also be used but can cause the decomposition of the anhydrides, particularly the low molecular weight anhydrides, such as acetic anhydride, and are not preferred for that reason. Phase transfer catalysis techniques may also be used, but the presence of water in connection with such techniques can also cause the lower molecular weight anhydrides to decompose.

It is preferred, as a matter of economy, to use at least 0.25 equivalents of alkali metal borohydride, since all 4 hydrogens of the alkali metal borohydride are active. The anhydride, on the other hand, is preferably used in excess (i.e., from about 5 to about 10 equivalents). The excess anhydride will be found helpful in preventing the reaction of acyl cyanide with itself.

The acyl cyanides which are used in the practice of the present invention are represented by the structural formula:

$$R_1-\overset{O}{\overset{\|}{C}}-CN$$

wherein $R_1$ represents an alkyl, alkenyl, cycloalkyl, aryl, aralkyl, alkylphenyl, phenyl ether, polyphenyl or heterocyclic radical, or a radical made up of any combination thereof; and may contain an inert substituent selected from the group consisting of halogen, alkyl and alkoxy; the radical having a total number of carbon atoms ranging from 1 to about 30. Preferably $R_1$ is an alkyl, alkoxyphenyl or phenoxyphenyl radical containing a total of from 1 to about 15 carbon atoms. Particularly preferred acyl cyanides for use in the practice of the present invention are meta-phenoxybenzoyl cyanide and benzoyl cyanide.

The anhydrides used in the practice of the present invention are represented by the structural formula:

$$R_2-\overset{O}{\overset{\|}{C}}-O-\overset{O}{\overset{\|}{C}}-R_2$$

wherein $R_2$ represents an alkyl, alkenyl, aryl or cycloalkyl radical or a radical comprised of any combination thereof; and may contain an inert substituent selected from the group consisting of halogen, alkyl and alkoxy; the radical having a total number of carbon atoms ranging from 1 to about 30, although 1 to about 10 carbon atoms are preferred.

Particularly preferred anhydrides used in the practice of the present invention are acetic anhydride, propionic anhydride, butyric anhydride and dichlorochrysanthemic anhydride; although acetic anhydride and dichlorochrysanthemic anhydride are especially preferred.

The alkali metal borohydrides used in the practice of the present invention include sodium borohydride, potassium borohydride and lithium borohydride; although sodium borohydride is preferred, because it is readily available.

The reaction will normally proceed without need for any special catalysts or temperature conditions once the reactive components are brought together in the reaction mixture.

The reaction is, however, exothermic and some cooling will generally be required. Preferably the reaction temperature is controlled within the range of from about $-20°$ C. to about $140°$ C., although temperatures ranging from about $0°$ C. to about $40°$ C. are most preferred.

In addition to using external cooling to control reaction temperature, the exotherm can be controlled by controlling the rate at which the alkali metal borohydride is added to the reaction mixture. If the alkali metal borohydride is added slowly, the reaction will proceed slowly and the exotherm will be relatively mild.

Typical of the process is the reaction between meta-phenoxybenzoyl cyanide, acetic anhydride and sodium borohydride. This reaction, when conducted under ambient conditions, can generally be completed in a time period of from about 0.5 to about 3 hours without external heating or cooling. Other combinations of reactants within the scope of the present invention will, in general, react in a similar manner, although the time required to complete the reaction will vary in accordance with the temperature at which the reaction is conducted, the particular reactants used and the relative concentration of each component in the reaction mixture.

The progress of the reaction may be followed by periodically withdrawing samples of the reaction mixture and determining the degree of conversion through infrared analysis. The reaction end-point will be indicated by a conversion approaching 100% of theoretical.

In order that the present invention be more fully understood, the following examples are given by way of illustration. No specific details or enumerations contained therein should be construed as limitations to the present invention except insofar as they appear in the appended claims. All parts and percentages are by weight unless otherwise specifically designated.

EXAMPLE 1

A solution of meta-phenoxybenzoyl cyanide (4.0 grams, 0.018 mole) in acetic anhydride (20 ml.) was prepared in a flask equipped with a magnetic stirrer. Finely ground sodium borohydride in an amount of 0.40 grams (0.011 mole) was added to the stirred solution. The temperature of the solution increased from 20° C. to 40° C. over a period of a few minutes; no external cooling was applied. About 30 minutes after the sodium borohydride was added the excess acetic anhydride was distilled off under reduced pressure.

The remaining contents of the flask were treated with dilute aqueous sodium carbonate solution and extracted with methylene chloride.

A 3.6 gram yield of final product liquid (75% of theory) was obtained. The spectral properties of this material were identical to those of a sample of meta-phenoxybenzaldehyde cyanohydrin acetate prepared from meta-phenoxybenzaldehyde cyanohydrin, acetyl chloride and triethylamine.

EXAMPLE 2

A solution of 3.0 g. (0.021 mole) meta-toluyl cyanide in 37 milliliters of acetic anhydride was placed in a flask which was equipped with a magnetic stirrer and cooled by a cold water bath. Finely ground sodium borohydride in the amount of 0.60 g. (0.016 mole) was gradually added to the stirred flask over a one-hour period, and stirring was maintained for an additional two hours. The flask contents were then distilled under reduced pressure to remove excess acetic anhydride. After the excess acetic anhydride was removed, a semi-solid residue remained in the flask.

Water and then methylene chloride were added to the flask, whereupon the semi-solid residue was dissolved.

The methylene chloride and water layers were then separated, and the methylene chloride fraction was washed with 5% sodium hydroxide solution.

The methylene chloride solvent was then evaporated to leave a pale yellow liquid residue. The pale yellow liquid was then purified by elution through a 6 inch by 1 inch silica gel column with diethyl ether.

The final product obtained amounted to 2.6 g. (62% of theoretical) of meta-tolualdehyde cyanohydrin acetate which was identified as such by infrared and nmr analysis.

What is claimed is:

1. A process for preparing cyanohydrin esters which comprises forming a reaction mixture of an acyl cyanide, a carboxylic acid anhydride and an alkali metal borohydride and reacting said reaction mixture at a temperature and for a time sufficient to form the cyanohydrin ester product of said acyl cyanide and carboxylic acid anhydride.

2. The process of claim 1 wherein said acyl cyanide is an acyl cyanide represented by the formula:

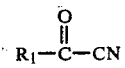

wherein $R_1$ represents an alkyl, alkenyl, cycloalkyl, aryl, aralkyl, alkylphenyl, diphenylether, polyphenyl or heterocyclic radical, or a radical comprised of any combination thereof; and has a total number of carbon atoms ranging from 1 to about 30.

3. The process of claim 2 wherein $R_1$ is an alkyl, alkoxyphenyl or phenoxyphenyl radical containing a total number of carbon atoms ranging from 1 to about 15.

4. The process of claim 1 wherein said acyl cyanide is meta-phenoxybenzoyl cyanide.

5. The process of claim 1 wherein said acyl cyanide is benzoyl cyanide.

6. The process of claim 1 wherein said anhydride is an anhydride represented by the formula:

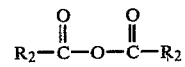

wherein $R_2$ represents an alkyl, aryl or cycloalkyl radical or a radical made-up of any combination thereof having a total number of carbon atoms ranging from 1 to about 30.

7. The process of claim 6 wherein said anhydride is acetic anhydride, propionic anhydride, butyric anhydride or dichlorochrysanthemic anhydride.

8. The process of claim 7 wherein said anhydride is acetic anhydride or dichlorochrysanthemic anhydride.

9. The process of claim 7 wherein said anhydride is acetic anhydride.

10. The process of claim 1 wherein said alkali metal borohydride is sodium borohydride.

11. A process for the preparation of meta-phenoxybenzaldehyde cyanohydrin acetate which comprises forming a reaction mixture of meta-phenoxybenzoyl cyanide, acetic anhydride and sodium borohydride and reacting said reaction mixture at a temperature and for a time sufficient to form meta-phenoxybenzaldehyde cyanohydrin acetate.

12. The process of claim 11 wherein said temperature ranges from 0° C. to about 40° C. and said time is from about 0.5 to about 3 hours.

13. A process for the preparation of benzaldehyde cyanohydrin acetate which comprises forming a reaction mixture of benzoyl cyanide, acetic anhydride and sodium borohydride and reacting said reaction mixture at a temperature and for a time sufficient to form benzaldehyde cyanohydrin acetate.

14. The process of claim 13 wherein said temperature ranges from 0° C. to about 40° C. and said time ranges from about 0.5 to about 3 hours.

* * * * *

UNITED STATES PATENT AND TRADEMARK OFFICE
CERTIFICATE OF CORRECTION

PATENT NO.   :   4,234,505
DATED        :   November 18, 1980
INVENTOR(S)  :   James M. Photis It is certified that error appears in the above-identified patent and that said Letters Patent are hereby corrected as shown below:

In the References - Kinishi et al. "43(4)" should be
-- 42(4) --.

Signed and Sealed this

Third Day of March 1981

[SEAL]

Attest:

RENE D. TEGTMEYER

Attesting Officer

Acting Commissioner of Patents and Trademarks